Sept. 27, 1960 H. M. TIRET Plant Pat. 1,973
FUCHSIA PLANT
Filed Oct. 27, 1959
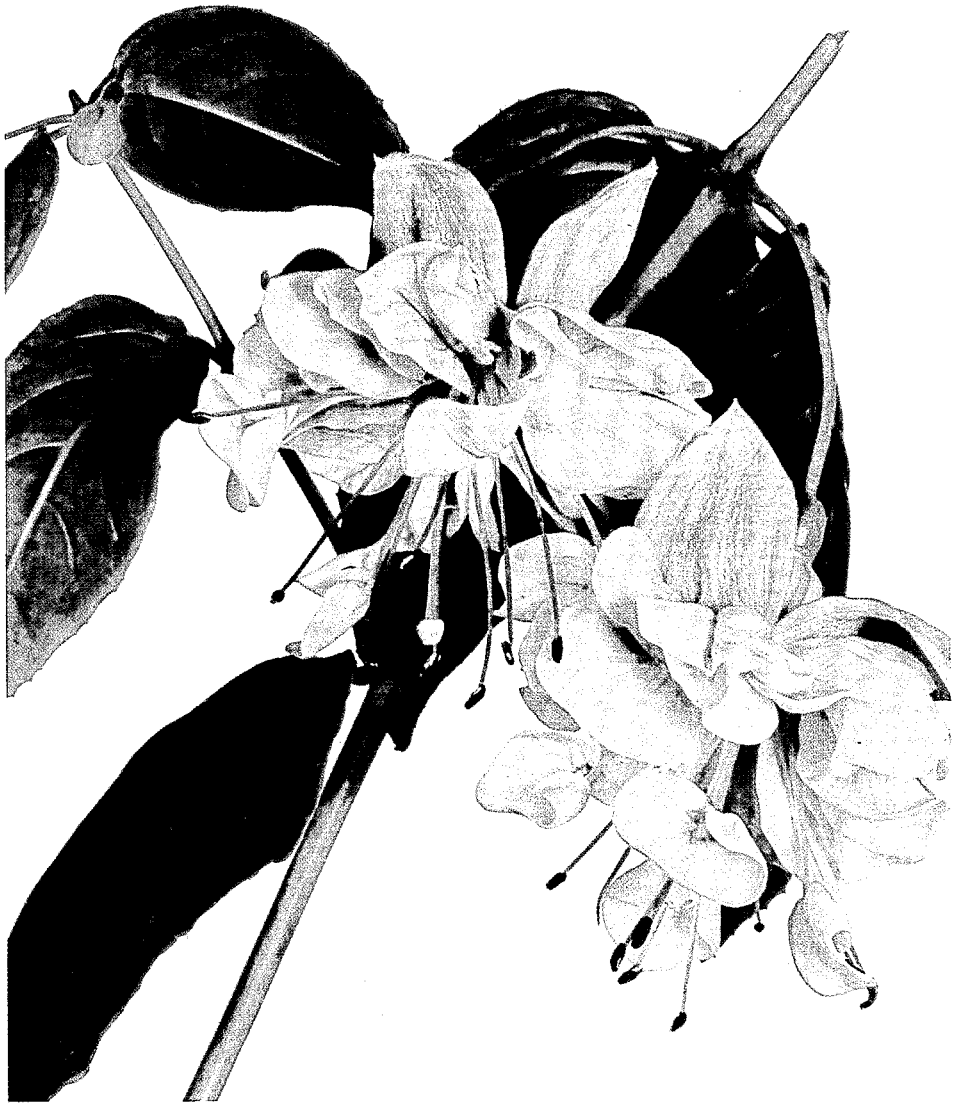

United States Patent Office

Plant Pat. 1,973
Patented Sept. 27, 1960

1,973

FUCHSIA PLANT

Horace M. Tiret, 2126 Taraval St.,
San Francisco 16, Calif.

Filed Oct. 27, 1959, Ser. No. 849,128

1 Claim. (Cl. 47—60)

This invention relates to a new and improved fuchsia plant, the principal new and different characteristics of which are the size and color of the flowers, combined with excellent form (4 protruding petaloids) and upright habit of growth, and featuring four hanging petaloids.

The accompanying color drawing illustrates the plant in bloom and the aforementioned new and different characteristic.

The plant was derived as a hybrid from seedling (unpatented) not introduced to the trade, namely 11/73/2 (applicant's breeding number) and seedling (unpatented) not introduced to the trade, breeding symbols unknown. The plant has been asexually reproduced at Colma, California, by cuttings which retained the characteristics of the parent fuchsia.

The plant is vigorous and upright in growing habit. It is very self-branching with medium-large foliage and large double dawn pink colored flowers. The flowers are produced in abundance. It is an early bloomer.

In the accompanying drawing, the figure shows a typical branch tip; the drawing representing approximate actual size.

A detailed description of this new variety of fuchsia plant follows:

*Habit of growth.*—Vigorous, upright, blooms early.

*Foliage.*—The foliage is medium-large in size, medium green in color. Leaves are heavily veined with serrated edges. Branches are reddish brown-green. The mature leaf is approximately 3½ inches in length and 2¼ inches in width at the widest point.

*Petals.*—The petals are Dawn Pink (British Horticultural Chart #523/3 and 523/2), 523/2 fading to 523/3. The petals are veined with Camellia Rose (B.H.C. #622). When the flower first grows the petals are #523/2 fading to 523/3 at maturity.

The petals number approximately 27, the entire corolla flares outward except the four center petaloids that hang down and surround the stamens. The petaloids, four in number, appear to be tiny petals attached to extra stamens. The diameter of the mature flower is approximately 2¾". Length of the large petals is 1¼," and the width, 1¼" (spread out). Appearance of the petals is smooth and veined.

*Ovary.*—Bright green in color. Length ½". Width of widest point ¼", when flower is fully open.

*Tube.*—Short and medium slender. Length ½". Width at widest point 5/16". Pale Camellia Rose (British Horticultural Chart #622/3).

*Sepals.*—Topside is Dawn Pink in color veined with Camellia Rose #622/2. Underside is crepelike in appearance and Camellia Rose #622 in color. The end of the sepal is Camellia Rose (#622/3) with pale green tips. Sepals are broad and short, recurving against tube. They are four in number. They are 1¼" in length and ¾" in width at widest point. Outerside is smooth and underside is crepelike.

*Stamens.*—Eight in number, Camellia Rose #622, with maroon colored anthers. Slender, with a length of 2" in the mature flower.

*Pistil.*—The style is approximately 1½" in length and 1/32" in width. It is Camellia Rose #622 in color and the stigma is creamy white.

*Buds.*—Camellia Rose #622 fading to 622/3 with green tips. Length from ovary is approximately 1½", and width at widest point 1¼".

*Parentage.*—Applicant's own seedling 11/73/2 (unpatented) not introduced to the trade, and seedling breeding symbols unknown, the figures representing applicant's own breeding symbols.

Having thus disclosed my discovery, I claim:

A new and different fuchsia plant herein described, characterized by the size, color and the unusual form of the fully open flower, showing four low petaloids hanging down from the other petals.

No references cited.